United States Patent [19]
Dohadwalla et al.

[11] Patent Number: 4,724,238
[45] Date of Patent: Feb. 9, 1988

[54] METHOD OF TREATING INFLAMMATORY DISEASES WITH LABDAN DERIVATIVES

[75] Inventors: Alihussein N. Dohadwalla; Sadashiv S. Mandrekar; Nandkumar K. Dadkar; Yatendra Khandelwal; Richard H. Rupp; Noel J. de Souza, all of Bombay, India

[73] Assignee: Hoechst Aktiengesellschaft, Fed. Rep. of Germany

[21] Appl. No.: 850,242

[22] Filed: Apr. 3, 1986

Related U.S. Application Data

[63] Continuation-in-part of Ser. No. 822,603, Jan. 27, 1986, abandoned.

[30] Foreign Application Priority Data

Jan. 26, 1985 [DE] Fed. Rep. of Germany ....... 3502686

[51] Int. Cl.$^4$ ............................................. A61K 31/35
[52] U.S. Cl. ..................................... 514/455; 549/389
[58] Field of Search ......................... 514/455; 549/389

[56] References Cited

U.S. PATENT DOCUMENTS

| | | | |
|---|---|---|---|
| 4,118,508 | 10/1978 | Bhat et al. | 514/455 |
| 4,134,986 | 1/1979 | Bajwa et al. | 514/455 |
| 4,517,200 | 5/1985 | Kreutner et al. | 514/455 |
| 4,564,626 | 1/1986 | Kreutner et al. | 514/455 |
| 4,578,399 | 3/1986 | Schorlemmer et al. | 514/455 |

FOREIGN PATENT DOCUMENTS

85/02616 6/1985 PCT Int'l Appl.

Primary Examiner—Nicky Chan
Attorney, Agent, or Firm—Finnegan, Henderson, Farabow, Garrett & Dunner

[57] ABSTRACT

The present invention relates to a process for the isolation of labdan derivatives from the plant Coleus forskohlii, and their use as medicaments having anti-inflammatory and analgesic activity.

4 Claims, No Drawings

METHOD OF TREATING INFLAMMATORY DISEASES WITH LABDAN DERIVATIVES

This application is a continuation-in-part of application Ser. No. 822,603, filed Jan. 27, 1986 now abandoned.

The invention relates to oxygenated labdane derivatives, to a process for their preparation and to their use as anti-inflammatory and analgesic agents.

The labdan derivative, Forskolin, namely $7\beta$-acetoxy-8,13-epoxy-$1\alpha,6\beta,9\alpha$-trihydroxy-labd-14-en-11one is described in German Offenlegungsschrift No. 2,557,784 and has the structure shown in formula I

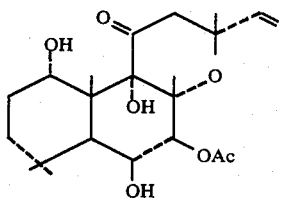

I 1,9-Dideoxyforskolin namely $7\beta$-acetoxy-1,9-dideoxy-8,13-epoxy-$6\beta$-hydroxy-labd-14-en-11-one has been described in Tetrahedron Letters No. 19, pp. 1669–1672, 1977 and has the structure shown in formula II

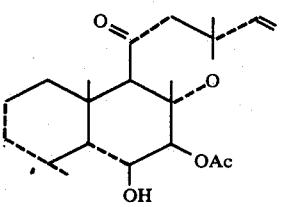

II

Other naturally-occurring forskolins are described in the above-mentioned publication, namely Tetrahedron Letters and in J. Med. Chem., 26 486 (1983); the compound coleforsin is described in German Offenlegungsschrift No. 26 40 275, synthetically-modified forskolins are described in J. Chem. Soc., Perkin Trans., 1, 767 (1982); J. Med. Chem., 26, 486 (1983) and German Offenlegungsschrift No. 26 54 796.

Oxygenated labdane derivatives of which forskolin is an example display interesting pharmacological properties that render them potentially suitable for use in the treatment of cardiac and circulatory diseases, hypertension, glaucoma, allergy, broncho-constriction and as immunostimulants (loc. cit. and German Patent DE No. 33 46 339, and German Offenlegungsschrift No. 33 14 999).

It has now been found that oxygenated labdane derivatives, surprisingly display anti-inflammatory and analgesic properties.

There is a continuing need for safe and effective anti-inflammatory agents. Inflammation is a disease process characterized by redness, fever, swelling and pain. Arthritis in its various forms, is the most prevalent, chronic and severe of the inflammatory diseases. Traumatic injury and infection also involves inflammation, and anti-inflammatory drugs are often used in their treatment. The usefulness of most commercial antiinflammatories is limited because of toxicity and adverse side effects. Many produce gastric irritation and other effects such as change in blood cells and central nervous system. Adrenocortical steroids produce gastric irritation and supression of normal adrenal function.

The present invention results from efforts to develop new antiarthritic compounds with good antiinflammatory activity and minimal side effects that could be more effective in treating arthritis than presently available drugs.

In addition to antiinflammatory properties, some compounds of this invention have demonstrated analgesic activity in a test procedure. This additional property is desirable in treatment of arthritis or related diseases; however, such compound can be employed solely to alleviate pain.

This invention provides oxygenated labdane derivatives, of which forskolin and 1,9-dideoxyforskolin are examples, as antiinflammatory and analgesic agents as well as processes for their preparation.

The present invention relates, thus, to the use of oxygenated labdane derivatives of the formula III

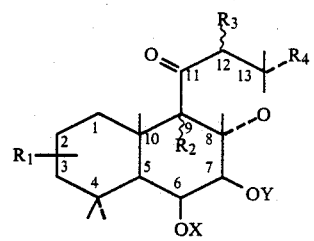

III wherein $R_1$, $R_2$, $R_3$ are the same or different and stand for H, OH, —O—OCR where R stands for $C_1$–$C_3$ alkyl groups, $R_1$ can occupy one or more of the positions 1–3 of the formula III; $R_4$ stands for CHO, CH=CH$_2$, CHOHCH$_2$OH, or

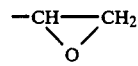

and X and Y stand for H or

where R has the aforementioned meanings, as inflammatory and analgesic agents. The preferred compounds of the invention are forskolin of the formula I, 1,9-dideoxyforskolin of the formula II and compound of the formula III wherein $R_1$, $R_2$, $R_3$ and X stand for H, Y stands for group

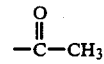

or H and $R_4$ for

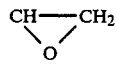

or CHOHCH$_2$OH.

The process by which forskolin is isolated from the plant, *Coleus forskohlii* is described in German OS No. 25 57 784.

The process by which 1,9-dideoxyforskolin is isolated from the plant, Coleus forskohlii, has till now not been described in detail. Its isolation has been briefly-indicated in the publication in Tet. Letters 19, 1669–1672 (1977). Accordingly, a feature of this invention is that it describes a process by which 1,9-dideoxyforskolin is isolated from the plant, Coleus forskohlii as represented by the following chart I herein below.

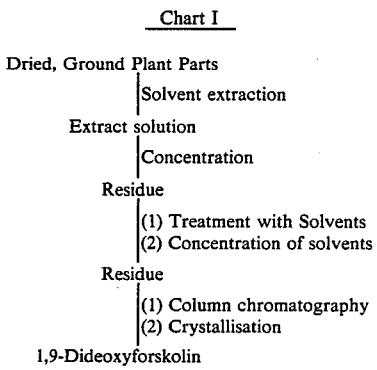

Chart I

Dried, Ground Plant Parts
 | Solvent extraction
Extract solution
 | Concentration
Residue
 | (1) Treatment with Solvents
 | (2) Concentration of solvents
Residue
 | (1) Column chromatography
 | (2) Crystallisation
1,9-Dideoxyforskolin It is suitable to use preferably the dried and ground roots of Coleus forskohlii.

For extracting the compound of the present invention from Coleus forskohlii, solvents such as aromatic hydrocarbons or aliphatic halogenated hydrocarbons having 1 to 3 carbon atoms and up to 3 halogen atoms, are preferably up to 3 chlorine atoms, or a lower alkanol having 1 to 6 carbon atoms are preferably used. From these solvents benzene, toluene, xylene, methylene chloride, chloroform, methanol and ethanol are preferred. The solvents are preferably used in the ratio of 2:1 to 10:1 parts by weight relative to the plant material. The extraction may be carried out at temperatures ranging from ambient to the boiling point of the solvent used for extraction, preferably, 30°–40° C. The extract solution is concentrated under reduced pressure, preferably in vacuo to give a residue. The residue is further treated with an organic solvent such as petroleum ether till the extraction is complete. The petroleum ether extract is further concentrated, preferably in vacuo to give a residue which is purified by column chromatography over silica gel and by crystallisation to obtain the 1,9-dideoxy-forskolin.

The compound of the invention $7\beta$-acetoxy-8,13,4,15-diepoxy-$6\beta$-hydroxy-labdan-11-one (formula III,

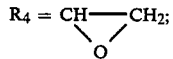

$R_4 = CH\underset{O}{-\!-\!-}CH_2;$ $R_1, R_2, R_3=H; X=H, Y=OAc$) is prepared by reacting 1,9-dideoxy forskolin with peracids such as m-chloroperbenzoic acid in halogenated hydrocarbons such as dichloromethane. Further treatment of this compound with alkali metal hydroxide such as sodium hydroxide in aqueous organic solvents such as dioxane:water gives the compound 8,13-epoxy$6\beta,7\beta$,14,15-tetrahydroxy-labdan-11-one (formula III $R_4$=CHOHCH$_2$OH; $R_1, R_2, R_3, X, Y=H$) which is purified by column chromatography.

A further feature of the invention is that the compound of the invention according to formula III, represented by forskolin and 1,9-dideoxyforskolin have displayed anti-inflammatory and analgesic properties in laboratory animals. Procedures for detecting and comparing the anti-inflammatory activity of the compounds of formula III and standard drugs, for which there is a good correlation with human efficacy, are the acute carrageenin-induced rat paw oedema test, croton oil-induced local inflammation test and adjuvant-induced arthritis test in rats.

(a) Acute carrageenin-induced rat paw oedema test

Charles Foster male rats (120–150 g) are fasted for 18 hrs. with water ad libitum. The test compound suspended in 0.5% carboxymethyl cellulose (CMC) is given intraperitoneally. The control group receives 0.5% CMC suspension. 0.05 ml of the 0.5% carrageenin suspension is injected subcutaneously into the planter region of the left hind paw. The paw volume is determined before carrageenin injection and at 3 hours and 6 hours after injection using a Maclab volume differential meter. The percentage decrease in paw volume is calculated with the following formula:

$$\frac{\text{Mean oedema volume (vehicle control)} - \text{mean oedema volume (test group)}}{\text{mean oedema volume (vehicle control)}} =$$

% increase in paw volume.

The ED$_{50}$ value is calculated from the dose-response curve. Six animals are used per group.

(b) Croton oil-induced local inflammation test in rats

A volume of 0.05 ml of croton oil irritant (2.0 ml pyridine, 0.5 ml distilled water+7.4 ml diethyl ether+0.1 ml croton oil) is applied under ether anaesthesia to the anterior and posterior sides of the ear of rats weighing 45 to 60 g (Charles Foster's strain) with the help of a micro glass syringe and a blunt 20 gauge needle/Tonelli G., Thibault L. and Ringer I, Endocrinology 77, 625–634 (1965)/.

The right untreated ear serves as control. The drug treated group receives different concentrations of compounds along with the irritant. Four hours later the animals are sacrificed.

The ears are removed and punched with an 8 mm diameter cork borer. The punched portions are immediately weighed. The increase in the weight of ear is determined by the difference in the weight between the left and right ear.

The topical anti-inflammatory activity of the test compound is expressed as the percent inhibition of the increase in ear weight of the irritant treated ear according to the following formula $$\frac{\text{Increase in weight of irritant treated ear} + \text{Increase in weight of irritant drug treated ear}}{\text{Increase in weight of irritant treated ear}} +$$

100 = % inhibition.

The ED$_{50}$ value is calculated from the dose response curve. Six animals are used per group.

(c) Adjuvant-induced arthritis test in rats

Female Charles Foster rats (180–200 g) are injected intradermally at the base of the tail with 0.1 ml of a 1% suspension of Mycobacterium tuberculum in mineral oil. Non-arthritic controls are injected with mineral oil. The volume of the left and right hind paw each rat is measured from the 7th day onwards, every day till 21 days using a Maclab volume differential meter. In the case of developing arthritis the test compound suspended in 0.5% carboxy methyl cellulose (CMC) is given intraperitoneally once daily for 21 days. In estabilished arthritis, however, the test compound suspended in 0.5% CMS is administered intraperitoneally once daily after the full development of the arthritis which is 15 days after the injection of the adjuvant, i.e. from day 15 to day 21.

The results obtained in these tests with the compounds of the invention are exemplified by forskolin and 1,9-dideoxyforskolin are provided in the following table.

| ANTIINFLAMMATORY AND ANALGESIC ACTIVITY OF FORSKOLIN AND 1,9-DIDEOXYFORSKOLIN | | |
|---|---|---|
| Activity | Forskolin | 1,9-Dideoxyforskolin |
| (a) Topical | | |
| Croton oil induced rat ear inflammation | $ED_{50}$: 1.15 mg/ear | $ED_{50}$: 1.6 mg/ear |
| (b) Systemic | | |
| Carrageenin induced rat paw oedema | $ED_{50}$: 4.80 mg/kg, i.p. | $ED_{50}$: 2.2 mg/kg, i.p. |
| (c) Adjuvant-induced arthritis in rats | | |
| Developing arthritis | 2.5 mg/kg, i.p. 23% inhibition | 3.0 mg/kg, i.p. 62% inhibition |
| Established arthritis | 2.4 mg/kg, i.p.: 27% inhibition | 3.0 mg/kg, i.p.: 30% inhibition |
| Analgesic activity | | |
| Acetic acid induced writhing in mice | | $ED_{50}$: 9.0 mg/kg, s.c. |

The percentage inhibition of the paw volume in developing arthritis is determined as follows:

$$\frac{\text{Mean paw volume change of untreated} - \text{Mean paw volume change of drug-treated}}{\text{Mean paw volume change of untreated}} \times 100 = \% \text{ inhibition of paw volume}$$

The percentage inhibition of the paw volume in established arthritis is determined as follows:

$$\frac{\text{Mean paw volume of untreated} - \text{Mean paw volume of drug treated}}{\text{Mean paw volume of untreated}} \times 100 \% = \text{inhibition of paw volume}$$

Analgesic activity—Acetic acid writhing test

A test compound suspended in 0.5% carboxy methyl cellulose is given subcutaneously to the male mice (20–25 g). The control group received only the 0.5% CMC. After 30 minutes, 0.2 ml of 3% acetic acid is administered intraperitoneally. The animals are observed for 15 minutes for a characteristic stretching or writhing syndrome which is indicative of pain induced by acetic acid. Six animals are used per group.

In the test group, mice which show less than or equal to 50 percent of the mean control writhing value are considered to be protected. (Blumberg et al. Proc. Soc. Exp. Biol. Med., 118, 763–766, 1965). The percent analgesic activity is calculated as follows:

$$\% \text{ analgesic activity} = \frac{\text{Number of protected mice}}{\text{Total number of mice}} \times 100$$

The $ED_{50}$ value is calculated from the dose response curve.

The compounds of the invention may be administered to treat arthritis or other inflammed conditions or to alleviate pain by any means that produces contact of the active agent with the agents site of action in the body of mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The usual forms of administration are oral in solid dosage forms, such as capsules, tablets, and powders, or in liquid dosage forms, such as elixirs, syrups, and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release of medicament over a period of hours. Compressed tablets can be sugar coated or film coated to make any unpleasant taste and protect the tablet from the atmosphere, or enteric coating for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Alone used are citric acid and its salts and sodium EDTA. In addition parenteral solutions can contain preservatives, such as benzalkonium chloride, methyl- or propylparaben and chlorobutanol.

Suitable pharmaceutical carriers are described in Remington's Pharmaceutical Sciences, E. W. Martin, a standard reference text in this field.

The amount of active compound in such a composition is such that a suitable dosage will be obtained. Preferred compositions and preparations according to the present invention are prepared so that an oral dosage unit form contains between 0.5–50 mg/kg body weight, and a parenteral dosage unit form contains between 0.05–10 mg/kg body weight of the active compound, preferably 0.1–5 mg/kg.

The following examples illustrate but do not limit the scope of the invention.

EXAMPLE 1

The dried and powdered roots of *Coleus forskohlii* (4 kg dry weight) were extracted three times repeatedly (20 l, 16 l, 16 l) with benzene at a temperatur of 35°–40° C. using a total volume of benzene (52 l). Completion of extraction was checked by observing that a negative color test was obtained for the presence of terpenoids (vanillin-sulphuric acid or anisaldehyde-sulfuric acid spray) on a TLC (Thin layer chromatography) plate after the successive extractions.

The benzene extracts were evaporated to dryness in vacuo at a temperature less than 40° C. The residue (0.2 kg) was triturated thrice (2 l each time) with a total volume of 6 l of petroleum ether (b.p. 60°–80° C.). The petroleum ether layer was separated, and evaporated to dryness in vacuo at a temperature less than 40° C. The residue (52 g) was subjected to column chromatography over silica gel to yield crude 1,9-dideoxy-forskolin which was crystallised from ethylacetate-pertroleum ether (1:9) to yield 1,9-dideoxyforskolin (1.2 g), m.p. 162°–65° C.

EXAMPLE 2

Dried and ground roots (12 kg) of *Coleus forskohlii* were extracted with 25 l portions of chloroform till they were exhaustively extracted. 75 l of chloroform were used. The combined chloroform extracts were filtered and evaporated in vacuo. The residue (ca. 300 g) was stirred thrice with 1.5 l portions of petroleum ether and filtered. The filtrate was evaporated to dryness to give a gummy residue (ca. 125 g). The residue was processed further as described in Example 1, to obtain 3.58 g of 1,9-dideoxyforskolin, m.p. 162°–65° C.

EXAMPLE 3

7-β-Acetoxy-8,13; 14,15-diepoxy-6β-hydroxy-labdan-11-one

A solution of m-chloroperbenzoic acid (2.0 g) in dry dichloromethane (50 ml) was added to the ice cooled solution of 1,9-dideoxyforskolin (2.0 g) in dry dichloromethane (150 ml). Reaction mixture was stirred for 20 hrs. Excess of m-chloroperbenzoic acid was decomposed by addition of aqueous sodium bisulphite solution to reaction mixture. Organic layer was separated, washed with aqueous sodium bicarbonate followed by water, dried over sodium sulphate and concentrated. Residue obtained was purified by flash chromatography using ethylacetate:benzene as eluent to obtain 7-β-acetoxy-8,13; 14,15-diepoxy-6β-hydroxy-labdan-11-one, m.p. 214°–17° C.

EXAMPLE 4

8,13-Epoxy-6β,7β,14,15-tetrahydroxy-labdan-11-one

7β-Acetxoy-8,13; 14,15-diepoxy-6β-hydroxy-labdan-11-one (0.6 g) was added to a solution of sodium hydroxide (0.3 g) in dioxane:water (1:1; 30 ml). Reaction mixture was stirred for 3 hours and then concentrated under vacuo at 80° C. Residue was extracted with ethylacetate. Ethylacetate extract was washed with water, dried over sodium sulphate and concentrated. Residue obtained was purified by flash chromatography using ethylacetate:petroleum ether as eluent to obtain 8,13 epoxy-6β,7β,14,15-tetrahydroxy-labdan-11-one, m.p. 193°–95° C.

We claim:

1. A method of treating inflammatory diseases which comprises administering to a mammal in need of such treatment an effective amount of a compound of the formula III

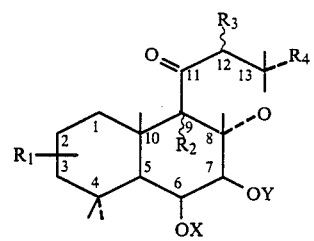

wherein $R_1$ is in the 1-position and represents H, OH, or —OCO—$C_1$–$C_3$-alkyl, $R_2$ is H or OH, $R_3$ is H, $R_4$ stands for —CHO, —CH=$CH_2$, —CHOHCH$_2$H or

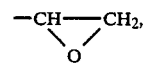

and X and Y stand for H or

where R stands for $C_1$–$C_3$-alkyl.

2. The method as defined in claim 1 wherein a compound of the formula III is administered wherein $R_1$ represents the 1-OH-group, $R_2$ represents OH, $R_3$ and X represent H, Y represents the residue

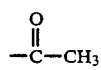

and $R_4$ represents the vinyl group.

3. The method as defined in claim 1 wherein a compound of the formula III is administered where $R_1$, $R_2$, $R_3$ and X represents H, Y represents the group

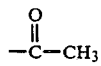

and $R_4$ represents the vinyl group.

4. A method for treating pain wich comprises the administration to a host in need of such treatment a therapeutically effective amount of 1,9-dideoxyforskolin.

* * * * *